United States Patent
Riedel et al.

[11] Patent Number: 6,069,264
[45] Date of Patent: May 30, 2000

[54] TRANSITION METAL COMPOUND

[75] Inventors: Michael Riedel, Essen; Gerhard Erker; Martin Könnemann, both of Münster, all of Germany

[73] Assignee: Targor GmbH, Germany

[21] Appl. No.: 08/874,024

[22] Filed: Jun. 12, 1997

[30] Foreign Application Priority Data

Jun. 14, 1996 [DE] Germany .............. 196 23 707

[51] Int. Cl.[7] ............................................ C07F 17/00
[52] U.S. Cl. .................... 556/53; 556/12; 556/20; 556/21; 556/22; 556/23
[58] Field of Search ............... 556/53, 12, 20, 556/21, 22, 23

[56] References Cited

U.S. PATENT DOCUMENTS

| | | | |
|---|---|---|---|
| 5,559,199 | 9/1996 | Abe et al. ............... | 526/160 |
| 5,565,534 | 10/1996 | Aulbach et al. ........ | 526/160 |
| 5,627,117 | 5/1997 | Mukaiyama et al. ... | 502/113 |

OTHER PUBLICATIONS

Journal of Organometallic Chemistry, 378, (1989) 153–161.

*Primary Examiner*—David W. Wu
*Assistant Examiner*—Ling-Siu Choi
*Attorney, Agent, or Firm*—Connolly, Bove, Lodge & Hutz LLP

[57] ABSTRACT

The present invention relates to a transition metal compound of the formula I

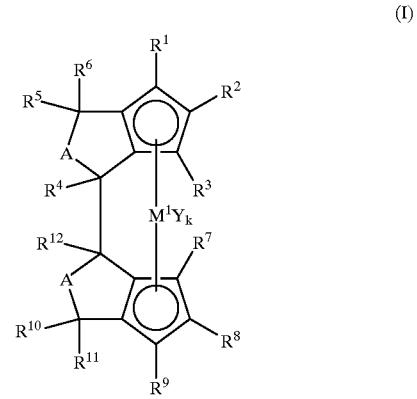

(I)

where
  $M^1$ is a transition metal of group IIIb, IVb, Vb or VIb of the Periodic Table of the Elements,
  Y are identical or different and are each a hydrogen atom, an OH group, a halogen atom, a $C_1$–$C_{40}$-hydrocarbon-containing group or an $NR^{15}_2$ group, where $R^{15}$ is a halogen atom, a $C_1$–$C_{10}$-alkyl group or a $C_6$–$C_{10}$-aryl group, k is an integer which corresponds to the valence of the transition metal atom $M^1$ minus two and, if Y is a butadiene unit, k is 1,
  $R^1$, $R^2$, $R^3$, $R^7$, $R^8$ and $R^9$ are identical or different and are each a hydrogen atom, a halogen atom, a $C_1$–$C_{40}$-hydrocarbon-containing group, an —$SiR^{15}_3$, —$NR^{15}_2$, —$SiOR^{15}_3$, —$SiSR^{15}_3$ or —$PR^{15}_2$ radical, where $R^{15}$ is a halogen atom, a $C_1$–$C_{10}$-alkyl group or a $C_6$–$C_{10}$-aryl group, or two or more adjacent radicals $R^1$, $R^2$ and $R^3$ or $R^7$, $R^8$ and $R^9$ together with the atoms connecting them form a ring system, $^1$H-NMR (200 MHz, $CD_2Cl_2$): 7.4–7.2 (m, 10H, Ph-H); 7.1–6.6 (m, 6H, Cp-H); 2.7 (m, 2H, $CH_2$); 1.9–0.8 (m, 6H, $CH_2$); 1.3 (s, 6H, $CH_3$); 1.2 (s, 6H, $CH_3$).

2 Claims, No Drawings

TRANSITION METAL COMPOUND

The present invention relates to a transition metal compound and a process for its preparation and also its use as a catalyst component in the preparation of polyolefins.

The preparation of polyolefins using soluble transition metal compounds and monocyclopentadienyl compounds in combination with aluminoxanes or other cocatalysts which, owing to their Lewis acidity, can convert the neutral transition metal compound into a cation and stabilize it is known from the literature (EP-A 129 368, EP-A 351 392, EP-A 416 815).

Transition metal compounds and monocyclopentadienyl compounds are of great interest not only in respect of the polymerization or oligomerization of olefins. They can also be used as hydrogenation, epoxidation, isomerization and C—C coupling catalysts (Chem. Rev. 1992, 92, 965–994).

Use of soluble transition metal compounds based on bis(cyclopentadienyl)zirconium dialkyls or dihalides in combination with oligomeric aluminoxanes gives atactic polymers which, owing to their unbalanced and unsatisfactory product properties, are of little industrial importance. In addition, certain olefin copolymers are not obtainable.

Derivatives of zirconocene dichloride in which the two substituted cyclopentadienyl groups are joined to one another via a methylene, ethylene or dimethylsilyl bridge can, owing to their conformational rigidity, be used as catalysts for the isospecific polymerization of olefins (EP-A 316 155).

J. Orgmet. Chem. 378 (1989), p.153 discloses the compound 8,8'-biguaiazulenetitanium dichloride.

It is an object of the present invention to make available new transition metal compounds.

The present invention accordingly provides a transition metal compound of the formula I Formula I

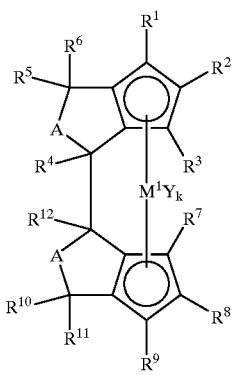

where
- $M^1$ is a transition metal of group IIIb, IVb, Vb or VIb of the Periodic Table of the Elements,
- Y are identical or different and are each a hydrogen atom, an OH group, a halogen atom, a $C_1$–$C_{40}$-hydrocarbon-containing group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-alkylaryl group, a $C_8$–$C_{40}$-arylalkenyl group or a substituted or unsubstituted butadiene unit, or an $NR^{15}_2$ group, where $R^{15}$ is a halogen atom, a $C_1$–$C_{10}$-alkyl group or a $C_6$–$C_{10}$-aryl group,
- k is an integer which corresponds to the valence of the transition metal atom $M^1$ minus two and, if Y is a butadiene unit, k is 1,
- $R^1$, $R^2$, $R^3$, $R^7$, $R^8$ and $R^9$ are identical or different and are each a hydrogen atom, a halogen atom, a $C_1$–$C_{40}$-hydrocarbon-containing group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-alkylaryl group, a $C_8$–$C_{40}$-arylalkenyl group, an —$SiR^{15}_3$, —$NR^{15}_2$, —$SiOR^{15}_3$, —$SiSR^{15}_3$ or —$PR^{15}_2$ radical, where $R^{15}$ is a halogen atom, a $C_1$–$C_{10}$-alkyl group or a $C_6$–$C_{10}$-aryl group, or two or more adjacent radicals $R^1$, $R^2$ and $R^3$ or $R^7$, $R^8$ and $R^9$ together with the atoms connecting them form a ring system which preferably contains from 4 to 40, particularly preferably from 6 to 20, carbon atoms,
- $R^4$, $R^5$, $R^6$, $R^{10}$, $R^{11}$ and $R^{12}$ are identical or different and are each a hydrogen atom, a halogen atom, a $C_1$–$C_{40}$-hydrocarbon-containing group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-alkylaryl group or a $C_8$–$C_{40}$-arylalkenyl group, an —$SiR^{15}_3$, —$NR^{15}_2$, —$SiOR^{15}_3$, —$SiSR^{15}_3$ or —$PR^{15}_2$ radical, where $R^{15}$ is a halogen atom, a $C_1$–$C_{10}$-alkyl group, or a $C_6$–$C_{10}$-aryl group, or two or more radicals $R^4$, $R^5$ and $R^6$ or $R^{10}$, $R^{11}$ and $R^{12}$ together with the atoms connecting them form a ring system which preferably contains from 4 to 40, particularly preferably from 6 to 20, carbon atoms, A is

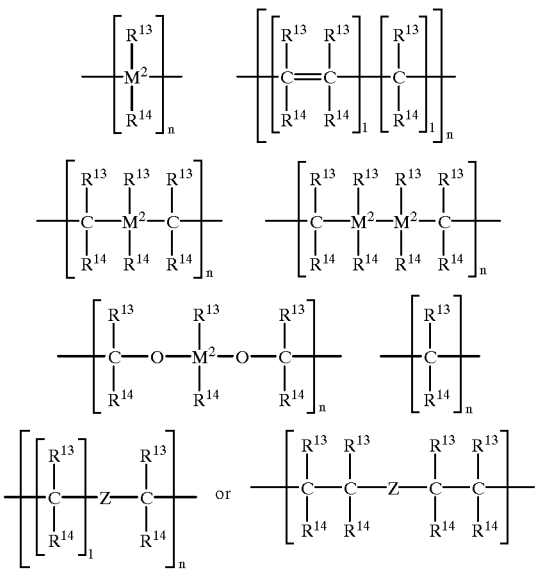

where
- n is an integer from 1 to 20, l is an integer from 1 to 20,
- Z is

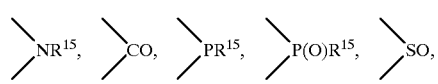

$SO_2$, O or S, where $R^{15}$ is a halogen atom, a $C_1$–$C_{10}$-alkyl group or a $C_6$–$C_{10}$-aryl group,
- $R^{13}$ and $R^{14}$ are identical or different and are each a hydrogen atom, a halogen atom or a $C_1$–$C_{40}$-hydrocarbon-containing group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-alkylaryl or a $C_8$–$C_{40}$- arylalkenyl group, or in each case two radicals $R^{13}$, in each case two radicals $R^{14}$, or in each case one radical $R^{13}$ and $R^{14}$, in each case together with the atoms connecting them, form a ring system and $M^2$ is silicon, germanium or tin, and the transition metal compound of the formula I is not 8,8'-biguaiazulenetitanium dichloride.

For the transition metal compound of the formula I, it is preferred that $M^1$ is a metal of group IVb of the Periodic Table of the Elements, Y are identical and, in particular, are each a $C_1$–$C_{10}$-hydrocarbon-containing group such as a $C_1$–$C_4$-alkyl group, or a substituted or unsubstituted, in particular an unsubstituted, butadiene unit or a halogen atom, in particular chlorine, $R^1$, $R^2$, $R^3$, $R^7$, $R^8$ and $R^9$ are identical or different and are each a hydrogen atom or a $C_1$–$C_{10}$-hydrocarbon-containing group such as a $C_1$–$C_{10}$-alkyl group or a $C_6$–$C_{10}$-aryl group, or two or more adjacent radicals $R^1$, $R^2$ and $R^3$ or $R^7$, $R^8$ and $R^9$ together with the atoms connecting them form a ring system which preferably contains from 6 to 20 carbon atoms, $R^4$, $R^5$, $R^6$, $R^{10}$, $R^{11}$ and $R^{12}$ are identical or different and are each a hydrogen atom, a halogen atom or a $C_1$–$C_{10}$-hydrocarbon-containing group such as a $C_1$–$C_{10}$-alkyl group, in particular $C_1$–$C_4$-alkyl group, or a $C_6$–$C_{10}$-aryl group, in particular $C_6$-aryl group, A is

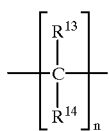

where n is an integer from 1 to 8, in particular 1, 2, 3 or 4, $R^{13}$ and $R^{14}$ are identical or different and are each a hydrogen atom or a $C_1$–$C_{10}$-hydrocarbon-containing group such as a $C_1$–$C_{10}$-alkyl group, in particular $C_1$–$C_4$-alkyl group, a $C_6$–$C_{10}$-aryl group, in particular $C_6$-aryl group, or in each case two radicals $R^{13}$, in each case two radicals $R^{14}$, or in each case one radical $R^{13}$ and $R^{14}$, in each case together with the atoms connecting them, form a hydrocarbon ring system which preferably contains from 6 to 10 carbon atoms.

Particular preference is given to transition metal compounds of the formula I in which $M^1$ is titanium or zirconium, Y are identical and are, in particular, methyl, phenyl or chlorine, $R^1$, $R^2$, $R^3$, $R^7$, $R^8$ and $R^9$ are identical or different and are each a hydrogen atom, a $C_1$–$C_4$-alkyl group such as methyl, ethyl, propyl, isopropyl, butyl, isobutyl or a $C_6$-aryl group such as phenyl, or $R^1$ and $R^2$ or $R^2$ and $R^3$ or $R^7$ and $R^8$ or $R^8$ and $R^9$ together with the atoms connecting them form an aromatic hydrocarbon ring system, e.g. a six-membered ring, which may in turn be substituted, A is

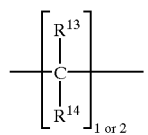

where $R^{13}$ and $R^{14}$ are identical or different and are each a hydrogen atom, a $C_1$–$C_4$-alkyl group such as methyl, ethyl, propyl, isopropyl, butyl, isobutyl or a $C_6$-aryl group such as phenyl, and the transition metal compound of the formula I particularly preferably has two identically substituted cyclopentadienyl ligands, so that the transition metal compound possesses symmetry.

The symmetry is preferably mirror symmetry (in the case of the meso form) or $C_2$ symmetry (in the case of the racemic form).

The nomenclature is illustrated by means of the following transition metal compound:

trans-4,4'-bis(4-phenyl-2,7,7-trimethyl-4,5,6,7-$\eta^5$-tetrahydroindenyl)zirconium dichloride:

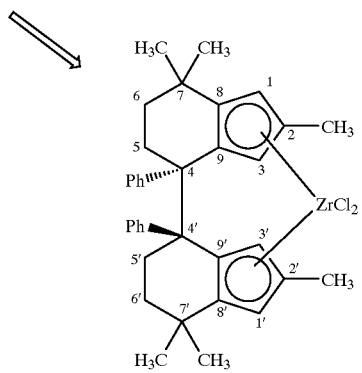

Examples of transition metal compounds of the invention having the formula I are:

trans-4,4'-bis(4-phenyl-2,7,7-trimethyl-4,5,6,7-$\eta^5$-tetrahydroindenyl)zirconium dichloride trans-4,4'-bis(4-phenyl-2,7,7-trimethyl-4,5,6,7-$\eta^5$-tetrahydroindenyl)zirconium dichloride trans-4,4'-bis(2-benzyl-4-phenyl-7,7-dimethyl-4,5,6,7-$\eta^5$-tetrahydroindenyl)zirconium dichloride trans-4,4'-bis(4,7,7-trimethyl-4,5,6,7-$\eta^5$-tetrahydroindenyl)zirconium dichloride trans-4,4'-bis(2-isopropyl-4,7,7-trimethyl-4,5,6,7-$\eta^5$-tetrahydroindenyl)zirconium dichloride trans-4,4'-bis(2-isopropyl-4,7,7-trimethyl-4,5,6,7-$\eta^5$-tetrahydroindenyl)dimethylzirconium trans-4,4'-bis(4-phenyl-2,7,7-trimethyl-4,5,6,7-$\eta^5$-tetrahydroindenyl)dimethylzirconium trans-4,4'-bis(2-benzyl-4-phenyl-7,7-dimethyl-4,5,6,7-$\eta^5$-tetrahydroindenyl)dimethylzirconium trans-4,4'-bis(2-isopropyl-4,7,7-trimethyl-4,5,6,7-$\eta^5$-tetrahydroindenyl)butadienezirconium trans-4,4'-bis(4-phenyl-2,7,7-trimethyl-4,5,6,7-$\eta^5$-tetrahydroindenyl)butadienezirconium trans-4,4'-bis(2-benzyl-4-phenyl-7,7-dimethyl-4,5,6,7-$\eta^5$-tetrahydroindenyl)butadienezirconium trans-4,4'-bis(4-methyl-4,5,6-η⁵-trihydropentalene)
zirconium dichloride trans-4,4'-bis(4-phenyl-4,5,6-η⁵-trihydropentalene)
zirconium dichloride trans-4,4'-bis(4-methyl-6-phenyl-4,5,6-η⁵-trihydropentalene)zirconium dichloride trans-4,4'-bis(4-methyl-6,6-diphenyl-4,5,6-η⁵-trihydropentalene)zirconium dichloride trans-4,4'-bis(4,6,6-triphenyl-4,5,6-η⁵-trihydropentalene)
zirconium dichloride trans-4,4'-bis(2-benzyl-4-methyl-4,5,6-η⁵-trihydropentalene)zirconium dichloride trans-4,4'-bis(2-isopropyl-4-phenyl-4,5,6-η⁵-trihydropentalene)zirconium dichloride trans-4,4'-bis(2,4-dimethyl-6-phenyl-4,5,6-η⁵-trihydropentalene)zirconium dichloride trans-4,4'-bis(2-isopropyl-4-methyl-6,6-diphenyl-4,5,6-η⁵-trihydropentalene)zirconium dichloride trans-4,4'-bis(2-methyl-4,6,6-triphenyl-4,5,6-η⁵-trihydropentalene)zirconium dichloride trans-4,4'-bis(4-methyl-4,5,6-η⁵-trihydropentalene)
dimethylzirconium trans-4,4'-bis(4-methyl-6-phenyl-4,5,6-η⁵-trihydropentalene)dimethylzirconium trans-4,4'-bis(2-isopropyl-4-methyl-4,5,6-η⁵-trihydropentalene)dimethylzirconium trans-4,4'-bis(4-methyl-4,5,6-η⁵-trihydropentalene)
butadienezirconium trans-4,4'-bis(4-methyl-6-phenyl-4,5,6-η⁵-trihydropentalene)butadienezirconium trans-4,4'-bis(2-isopropyl-4-methyl-4,5,6-η⁵-trihydropentalene)butadienezirconium The preparation of the transition metal compounds of the invention is demonstrated by the following reaction scheme.

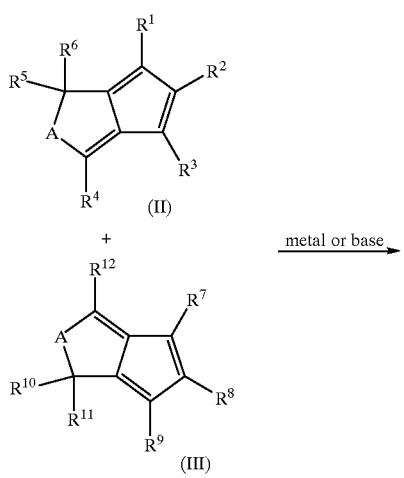

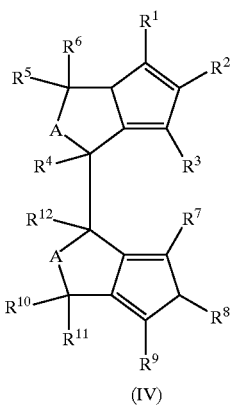

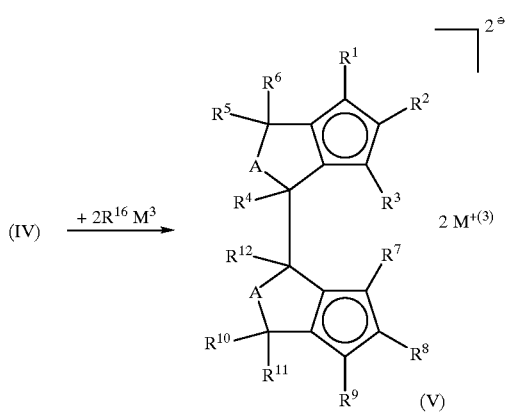

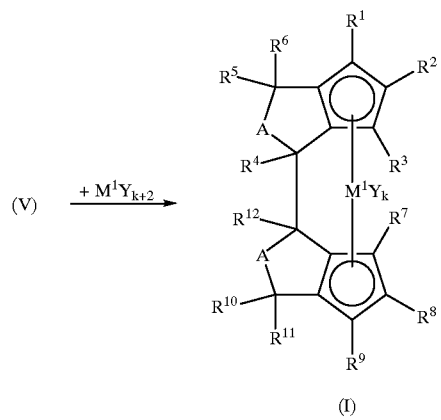

The compounds of the formulae (II) and (III) can be prepared by methods known from the literature (J. Org. Chem. 1995, 60, 813; J. Org. Chem. 1989; Chem. Ber. 1990, 123, 549; Angew. Chem. 1970, 82, 877; Tetrahedron Lett. 1977, 639). The reaction of the compounds of the formulae (I) and (II) to give the compounds (IV) is known in principle (Angew. Chem. 1993, 105, 1103; Helv. Chim. Acta 1993, 76, 1457; Angew. Chem. Int. Edit.1991, 30, 693). The deprotonation of the compound (IV) can be carried out using any base $R^{16}M^3$, where $M^3$ is a metal of group Ia or IIa of the Periodic Table of the Elements and $R^{16}$ is a $C_1$–$C_{10}$-hydrocarbon-containing group such as a $C_1$–$C_{10}$-alkyl, $C_6$–$C_{10}$-aryl or $C_1$–$C_{10}$-alkoxy group. In particular, the deprotonation can be carried out using dibutylmagnesium, methyllithium, butyllithium, lithium bishexamethyldisilazide or potassium tert-butoxide. The reaction of the compound (V) formed by this deprotonation with the corresponding metal compound $M^1Y_{k+2'}$, where k is an integer from 1 to 3 (e.g. vanadium trichloride, zirconium tetrachloride, niobium pentachloride) in an inert solvent is known in principle and leads to the formation of the transition metal compound of the invention (I).

Suitable inert solvents are aliphatic or aromatic solvents such as hexane or toluene, ether solvents such as tetrahydrofuran or diethyl ether or halogenated hydrocarbons such as methylene chloride or halogenated aromatic hydrocarbons such as o-dichlorobenzene.

The biscyclopentadienyl compounds of the formula (IV), in which at least one of the radicals $R^1$ to $R^3$ and also at least one of the radicals $R^7$ to $R^9$ is hydrogen can be reacted by methods known from the literature to give the fulvenes of the formula (VI). This is illustrated by the following scheme, where $R^{17}$ and $R^{18}$ are identical or different and are as defined for $R^4$.

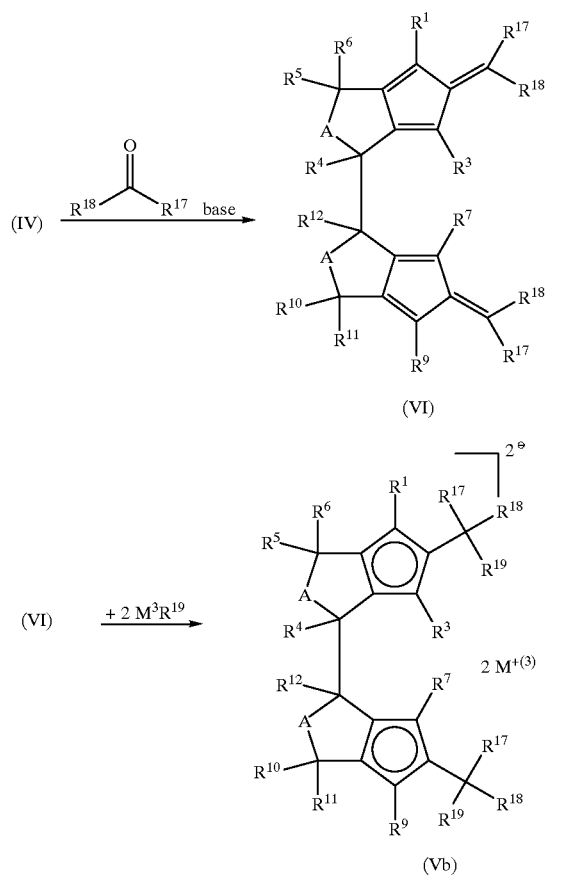

Reaction of the fulvene of the formula (VI) with two equivalents of an organometallic compound of the formula $R^{19}M^3$ (where $R^{17}$, $R^{18}$ and $R^{19}$ are identical or different and are as defined for $R^4$) leads to the formation of the dianion compound (Vb). The conversion into the transition metal compounds of the formula (I) is carried out similarly to the reaction from (V) to (I).

A further possibility for preparing coupling precursors of the formula (II) in which A is $CH_2$—$CH_2$ is illustrated in the following reaction scheme. Here, $M^4$ is a metal of group Ib or IIb, particularly preferably Ib, and $M^5$ is a metal of group Ia of the Periodic Table of the Elements.

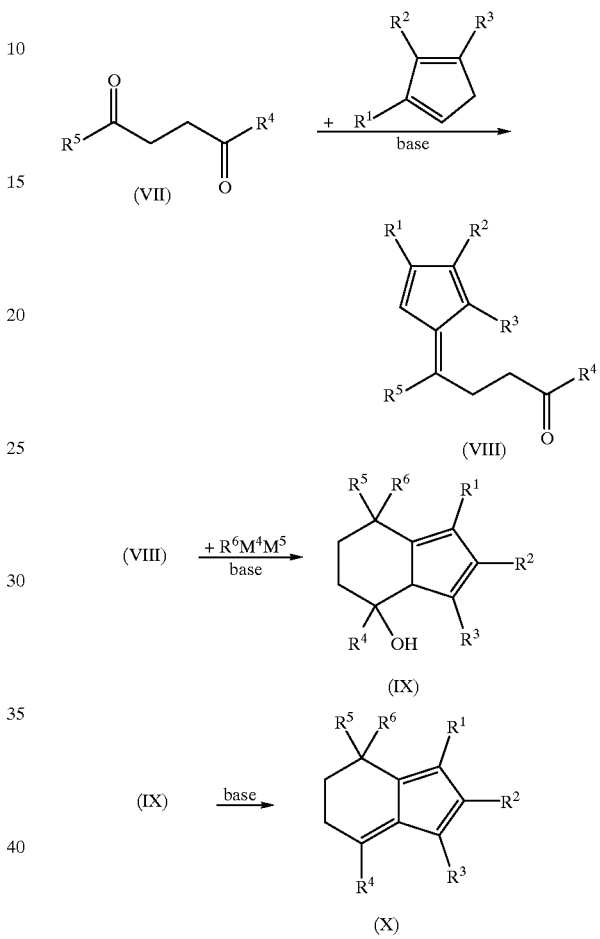

The symbols used in the formulae II to X are as defined for formula I.

The transition metal compounds of the invention are highly active catalyst components for olefin polymerization. Depending on the substitution pattern of the ligands, the transition metal compounds can occur as a mixture of isomers. The transition metal compounds are preferably used as pure isomers. The use of the racemate is sufficient in most cases.

The present invention also provides a process for preparing an olefin polymer by polymerization of one or more olefins in the presence of a catalyst comprising at least one transition metal compound of the formula I and at least one cocatalyst. The polymerization can be a homopolymerization or copolymerization.

In the process of the invention, preference is given to homopolymerizing or copolymerizing one or more olefins of the formula $R^a$—CH=CH—$R^b$, where $R^a$ and $R^b$ are identical or different and are each a hydrogen atom or a hydrocarbon radical having from 1 to 20 carbon atoms, in particular from 1 to 10 carbon atoms, or $R^a$ and $R^b$ together with the atoms connecting them form one or more rings. Examples of such olefins are 1-olefins such as ethylene, propylene, 1-butene, 1-pentene, 1-hexene, 4-methyl-1-pentene or 1-octene, styrene, cyclic and acyclic dienes such as 1,3-butadiene, isoprene, 1,4-hexadiene, norbornadiene, vinylnorbornene or 5-ethylidenenorbornene. In the process of the invention, preference is given to homopolymerizing ethylene or propylene or copolymerizing ethylene and propylene with one another and/or with one or more 1-olefins having from 4 to 20 carbon atoms and/or one or more dienes having from 4 to 20 carbon atoms, for example 1,3-butadiene.

The polymerization is preferably carried out at a temperature of from −60 to 250° C., particularly preferably from 50 to 200° C. The pressure is preferably from 0.5 to 2000 bar, particularly preferably from 5 to 64 bar.

The polymerization can be carried out in solution, in bulk, in suspension or in the gas phase, continuously or batchwise, in one or more stages. A preferred embodiment is suspension or gas-phase polymerization.

The catalyst used in the process of the invention preferably comprises one transition metal compound. It is also possible to use mixtures of two or more transition metal compounds, e.g. for preparing polyolefins having a broad or multimodal molecular weight distribution.

In principle, a suitable cocatalyst in the process of the invention is any compound which, owing to its Lewis acidity, can convert the neutral transition metal compound into a cation and stabilize the latter ("labile coordination"). In addition, the cocatalyst or the anion formed from it should undergo no further reaction with the transition metal compound cation formed (EP 427 697). The cocatalyst used is preferably an aluminum compound and/or a boron compound.

The boron compound preferably has the formula $R^{20}_x NH_{4-x} BR^{21}_4$, $R^{20}_x PH_{4-x} BR^{21}_4$, $R^{20}_3 CBR^{21}_4$ or $BR^{21}_3$, where x is a number from 1 to 4, preferably 3, the radicals $R^{20}$ are identical or different, preferably identical, and are $C_1$–$C_{10}$-alkyl or $C_6$–$C_{18}$-aryl, or two radicals $R^{20}$ together with the atoms connecting them form a ring, and the radicals $R^{21}$ are identical or different, preferably identical, and are $C_6$–$C_{18}$-aryl which may be substituted by alkyl, haloalkyl or fluorine. In particular, $R^{20}$ is ethyl, propyl, butyl or phenyl and $R^{21}$ is phenyl, pentafluorophenyl, 3,5-bistrifluoromethylphenyl, mesityl, xylyl or tolyl (EP 277 003, EP 277 004 and EP 426 638).

The cocatalyst used is preferably an aluminum compound such as aluminoxane and/or an aluminum alkyl.

The cocatalyst used is particularly preferably an aluminoxane, in particular of the formula XIa for the linear type and/or the formula XIb for the cyclic type,

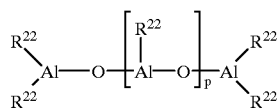
(XIa)

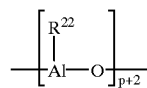
(XIb)

where, in the formulae XIa and XIb the radicals $R^{22}$ are identical or different and are each hydrogen or a $C_1$–$C_{20}$-hydrocarbon group such as a $C_1$–$C_{18}$-alkyl group, a $C_6$–$C_{18}$-aryl group such as phenyl or benzyl, and p is an integer from 2 to 50, preferably from 10 to 35.

The radicals $R^{22}$ are preferably identical and are hydrogen, methyl, isobutyl, phenyl or benzyl, particularly preferably methyl.

If the radicals $R^{22}$ are different, they are preferably methyl and hydrogen or alternatively methyl and isobutyl, where hydrogen or isobutyl are preferably present in a numerical proportion of from 0.01 to 40% (of the radicals $R^{22}$).

The methods of preparing the aluminoxanes are known. The exact spatial structure of the aluminoxanes is not known (J. Am. Chem. Soc. (1993) 115, 4971). For example, it is conceivable that chains and rings join to form larger two-dimensional or three-dimensional structures.

Regardless of the method of preparation, all aluminoxane solutions have in common a variable content of unreacted aluminum starting compound which is present in free form or as adduct.

It is possible to preactivate the transition metal compound using a cocatalyst, in particular an aluminoxane, before use in the polymerization reaction. This significantly increases the polymerization activity. The preactivation of the transition metal compound is preferably carried out in solution. Here, the transition metal compound is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The transition metal compound can be used in the same concentration, but it is preferably used in an amount of from $10^{-4}$ to 1 mol per mol of aluminoxane. The preactivation time is from 5 minutes to 60 hours, preferably from 5 to 60 minutes. The preactivation is carried out at a temperature of from −78 to 150° C., preferably from 0 to 80° C.

The transition metal compound is preferably employed in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The aluminoxane is preferably used in a concentration of from $10^{-6}$ to $10^{-1}$ mol, preferably from $10^{-5}$ to $10^{-2}$ mol, per $dm^3$ of solvent or per $dm^3$ of reactor volume. The other cocatalysts mentioned are used in approximately equimolar amounts to the transition metal compound. However, higher concentrations are also possible in principle.

The aluminoxane can be prepared in various ways by known methods. One of the methods is, for example, to react an aluminum hydrocarbon compound and/or a hydridoaluminum hydrocarbon compound with water (gaseous, solid, liquid or bound, for example as water of crystallization) in an inert solvent (for example toluene). To prepare an aluminoxane having different radicals $R^{24}$, for example, two different trialkylaluminums corresponding to the desired composition are reacted with water.

To remove catalyst poisons present in the olefin, purification using an aluminum compound, preferably an aluminum alkyl such as trimethylaluminum or triethylaluminum, is advantageous. This purification can be carried out either in the polymerization system itself or the olefin is brought into contact with the aluminum compound and subsequently separated off again before addition to the polymerization system.

As molecular weight regulator and/or to increase the catalyst activity, hydrogen can be added in the process of the invention. This enables low molecular weight polyolefins such as waxes to be obtained.

In the process of the invention, the transition metal compound is preferably reacted with the cocatalyst outside the polymerization reactor in a separate step using a suitable solvent. Application to a support can be carried out during this procedure.

In the process of the invention, a prepolymerization can be carried out with the aid of the transition metal compound. For the prepolymerization, preference is given to using the (or one of the) olefin(s) used in the polymerization.

The catalyst used in the process of the invention can be supported.

Application to a support enables, for example, the particle morphology of the polyolefin produced to be controlled. Here, the transition metal compound can be reacted first with the support and subsequently with the cocatalyst. The cocatalyst can also first be supported and subsequently reacted with the transition metal compound. It is also possible to support the reaction product of transition metal compound and cocatalyst. Suitable support materials are, for example, silica gels, aluminum oxides, solid aluminoxane or other inorganic support materials such as magnesium chloride. Another suitable support material is a polyolefin powder in finely divided form. The preparation of a supported cocatalyst can be carried out as described, for example, in EP 567 952.

The cocatalyst, e.g. aluminoxane, is preferably applied to a support such as silica gels, aluminum oxides, solid aluminoxane, other inorganic support materials or a polyolefin powder in finely divided form and then reacted with the transition metal compounds.

Inorganic supports which can be used are oxides which have been produced flame-pyrolytically by combustion of element halides in a hydrogen/oxygen flame, or can be prepared as silica gels in particular particle size distributions and particle shapes.

The preparation of a supported cocatalyst can be carried out, for example, as described in EP 578 838 in the following manner in a stainless steel reactor having an explosionproof design, a pumped circulation system and a pressure rating of 60 bar, with inert gas supply and cooling by means of jacket cooling and a second cooling circuit via a heat exchanger on the pumped circulation system. The pumped circulation system draws in the reactor contents through a connection in the bottom of the reactor by means of a pump and pushes it into a mixer and through a riser line via a heat exchanger back into the reactor. The mixer is configured such that in the inlet section there is a constricted tube cross-section where an increased flow velocity occurs and into whose turbulence zone there is conducted, axially and against the flow direction, a thin line through which, pulsed, a defined amount of water under 40 bar of argon can be fed in. The reaction is monitored via a sampler on the pumped circuit. In principle, other reactors are also suitable.

Further possible ways of preparing a supported cocatalyst are described in EP 578 838. The transition metal compound of the invention is then applied to the supported cocatalyst by stirring the dissolved transition metal compound with the supported cocatalyst. The solvent is removed and replaced by a hydrocarbon in which both cocatalyst and the transition metal compound are insoluble.

The reaction to give the supported catalyst system is carried out at a temperature of from −20 to +120° C., preferably from 0 to 100° C., particularly preferably from 15 to 40° C. The transition metal compound is reacted with the supported cocatalyst by combining a 1–40% strength by weight, preferably 5–20% strength by weight, suspension of the cocatalyst in an aliphatic, inert suspension medium such as n-decane, hexane, heptane or diesel oil with a solution of the transition metal compound in an inert solvent such as toluene, hexane, heptane or dichloromethane or with the finely milled solid of the transition metal compound. The other way around, a solution of the transition metal compound can also be reacted with the solid of the cocatalyst.

The reaction is carried out by intensive mixing, for example by stirring at a molar $Al/M^1$ ratio of from 100/1 to 10,000/1, preferably from 100/1 to 3000/1, and a reaction time of from 5 to 120 minutes, preferably from 10 to 60 minutes, particularly preferably from 10 to 30 minutes, under inert conditions.

During the course of the reaction time for preparing the supported catalyst system, changes in the color of the reaction mixture occur, particularly when using transition metal compounds of the invention having absorption maxima in the visible region, and these enable the progress of the reaction to be followed.

After the reaction time has elapsed, the supernatant solution is separated off, for example by filtration or decantation. The remaining solid is washed from 1 to 5 times with an inert suspension medium such as toluene, n-decane, hexane, diesel oil or dichloromethane to remove soluble constituents in the catalyst formed, in particular to remove unreacted and therefore soluble transition metal compound.

The supported catalyst system thus prepared can be resuspended as vacuum-dried powder or while still moist with solvent and metered into the polymerization system as a suspension in one of the abovementioned inert suspension media.

If the polymerization is carried out as a suspension or solution polymerization, use is made of an inert solvent customary for the Ziegler low-pressure process. For example, it is carried out in an aliphatic or cycloaliphatic hydrocarbon; examples of such hydrocarbons are propane, butane, hexane, heptane, isooctane, cyclohexane and methylcyclohexane. It is also possible to use a petroleum fraction or hydrogenated diesel oil fraction. Toluene can also be used. Preference is given to carrying out the polymerization in the liquid monomer.

Before addition of the catalyst, in particular the supported catalyst system (comprising a transition metal compound of the invention and a supported cocatalyst or comprising a transition metal compound of the invention and an organoaluminum compound on a polyolefin powder in finely divided form), another aluminum alkyl compound such as—trimethylaluminum, triethylaluminum, triisobutylaluminum, trioctylaluminum or isoprenylaluminum can be additionally introduced into the reactor to make the polymerization system inert (for example to remove catalyst poisons present in the olefin). This is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This enables a small molar $Al/M^1$ ratio to be selected in the synthesis of a supported catalyst system.

If inert solvents are used, the monomers are metered in in gaseous or liquid form.

The time of the polymerization can be selected freely, since the catalyst system to be used in the process of the invention displays only a small time-dependent drop in the polymerization activity.

The following examples illustrate the invention.

Preparation and handling of organometallic compounds were carried out with exclusion of air and moisture under argon (Schlenk technique). All solvents required were made absolute before use by boiling for a number of hours over a suitable desiccant and subsequent distillation under argon.

The compounds were characterized by $^1$H-NMR, $^{13}$C-NMR- and IR spectroscopy.

EXAMPLE 1 trans-4,4'-Bis(4-phenyl-7,7-dimethyl-4,5,6,7-η⁵-tetrahydroindenyl)zirconium dichloride 1-Phenyl-4-(2',4'-cyclopentadien-1'-ylidene)pentan-1-one Under protective gas, 6.6 ml (83.8 mmol) of cyclopentadiene are added dropwise to a solution of 9.8 g (55.6 mmol) of 1-phenyl-1,4-pentadione in about 700 ml of methanol. 13.7 ml (174 mmol) of pyrrolidine are subsequently added. The solution is stirred for 2 hours and subsequently acidified using glacial acetic acid. The product is extracted with diethyl ether, dried over $MgSO_4$ and the solvent is removed under reduced pressure. Crystallization from diethyl ether gives the product in a 50% yield in the form of yellow needles.

$^1$H-NMR (200 MHz, $CDCl_3$): 7.9–7.3 (m, 5H, Ph-H); 6.5 (s, 4H, Cp-H); 3.3–2.7 (m, 4H, $CH_2$); 2.2 (s, 3H, $CH_3$).

7,7-Dimethyl-4-phenyl-4,5,6,7-tetrahydroinden-cis-4-ol 6.3 g (26 mmol) of 1-phenyl-4-(2',4'-cyclopentadien-1'-ylidene)pentan-1-one are dissolved in 300 ml of diethyl ether and a solution of $Me_2CuLi$ (prepared from 11.2 g of CuI, 250 ml of diethyl ether, 65 ml of a 1.8 molar MeLi solution) is added dropwise over a period of 10 minutes. The suspension is stirred for another 4 hours and subsequently hydrolyzed with water. The aqueous phase is extracted with diethyl ether, the combined ether phases are washed with water, dried over $MgSO_4$ and the solvent is subsequently removed under reduced pressure. The product is obtained in a 93% yield.

$^1$H-NMR (200 MHz, $CDCl_3$): 7.6–7.2 (m, 5H, Ph-H); 6.5; 6.1; 5.9 (each m, each 1H, Cp-H); 3.6 (s, 1H, OH); 2.3–2.1 (m, 1H, CH); 1.9–1.5 (m, 4H, $CH_2$); 1.3 (s, 3H, $CH_3$); 1.2 (s, 3H, $CH_3$).

7,7-Dimethyl-4-phenyl-(1,3-dienylidene)-4,5,6,7-tetrahydroindene

A solution of 2.9 g (27 mmol) of lithiumdiisopropylamide in 100 ml of tetrahydrofuran is added dropwise at –30° C. to a solution of 6.2 g (26 mmol) of 7,7-dimethyl-4-phenyl-4,5,6,7-tetrahydroinden-cis-4-ol in 200 ml of diethyl ether. The solution is stirred for 12 hours at room temperature, hydrolyzed with water and the product is extracted with diethyl ether. After drying over $MgSO_4$ and removal of the solvent under reduced pressure, the product is obtained in a 97% yield.

$^1$H-NMR (200 MHz, $CDCl_3$): 7.5–7.3 (m, 5H, Ph-H); 6.5; 6.2; 6.1 (each m, each 1H, Cp-H); 2.8 (t, 2H, $CH_2$); 1.8 (t, 2H, $CH_2$); 1.2 (s, 6H, $CH_3$).

4,4'-Bis(7,7-dimethyl-4-phenyl-4,5,6,7-tetrahydroindene)

300 mg (1.1 mmol) of $HgCl_2$ are added to 1 g (25 mmol) of granulated calcium in 200 ml of tetrahydrofuran. The mixture is stirred at room temperature, 0.2 g of mercury is added and stirring is continued for another 12 hours. The solution is cooled to –30° C. and a solution of 2.0 g (9 mmol) of 7,7-dimethyl-4-phenyl-(1,3-dienylidene)-4,5,6,7-tetrahydroindene in 40 ml of tetrahydrofuran is added dropwise over a period of 10 minutes. After stirring for 12 hours, the reaction mixture is hydrolyzed and the product is extracted with diethyl ether. Drying over $MgSO_4$ and removing the solvent under reduced pressure gives a 98% yield of the product which is in the form of double-bond isomers but in the bridging position has, stereoselectively, only one translinkage.

$^1$H-NMR (200 MHz, $CDCl_3$): 7.5–7.0 (m, 10H, Ph-H); 6.7–5.9 (m, 4H, Cp-H); 3.1–2.6 (m, 4H, $CH_2$); 2.2–0.9 (m, 8H, $CH_2$); 1.2 (s, 6H, $CH_3$); 0.8 (s, 6H, $CH_3$).

trans-4,4'-Bis(4-phenyl-7,7-dimethyl-4,5,6,7-η5-tetrahydroindenyl)zirconium dichloride 5.7 ml of a 1.6 molar solution of n-butyllithium in toluene are added to a solution of 1.2 g (4.4 mmol) of 4,4'-bis(7,7-dimethyl-4-phenyl-4,5,6,7-tetrahydroindene) in 100 ml of toluene and the solution is stirred for 4 hours. 1.0 g of zirconium tetrachloride is subsequently added and the solution is stirred for 12 hours. The lithium chloride is separated off by filtration and the filtrate is evaporated to dryness under reduced pressure and subsequently taken up with pentane. The suspension is filtered and the violet powder is characterized by NMR spectroscopy.

$R^4$, $R^5$, $R^6$, $R^{10}$, $R^{11}$ and $R^{12}$ are identical or different and are each a hydrogen atom, a halogen atom, a $C_1$–$C_{40}$-hydrocarbon-containing group, an —$SiR^{15}_3$, —$NR^{15}_2$, —$SiOR^{15}_3$, —$SiSR^{15}_3$ or —$PR^{15}_2$ radical, where $R^{15}$ is a halogen atom, a $C_1$–$C_{10}$-alkyl group, or a $C_6$–$C_{10}$-aryl group, or two or more radicals $R^4$, $R^5$ and $R^6$ or $R^{10}$, $R^{11}$ and $R^{12}$ together with the atoms connecting them form a ring system, A is

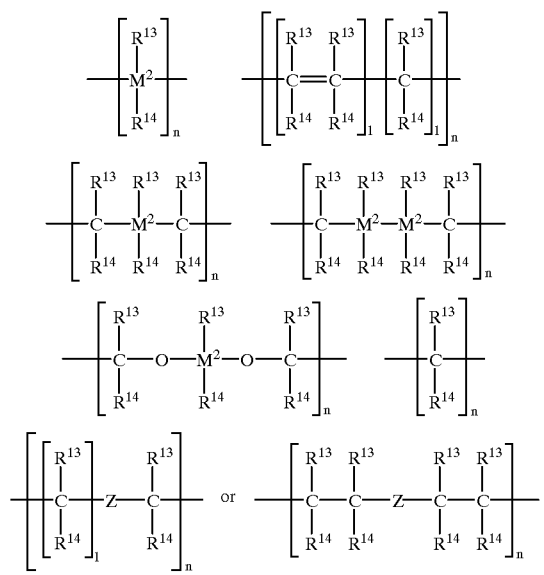

where n is an integer from 1 to 20, l is an integer from 1 to 20,

Z is

$SO_2$, O or S, where $R^{15}$ is a halogen atom, a $C_1$–$C_{10}$-alkyl group or a $C_6$–$C_{10}$-aryl group, $R^{13}$ and $R^{14}$ are identical or different and are each a hydrogen atom, a halogen atom or a $C_1$–$C_{40}$-hydrocarbon-containing group or in each case two radicals $R^{13}$, in each case two radicals $R^{14}$, or in each case one radical $R^{13}$ and $R^{14}$, in each case together with the atoms connecting them, form a ring system and $M^2$ is silicon, germanium or tin, and the transition metal compound of the formula I is not 8,8'-biguaiazulenetitanium dichloride.

The transition metal compound is suitable as a catalyst component for olefin polymerization.

What is claimed is:

1. A transition metal compound of the formula I

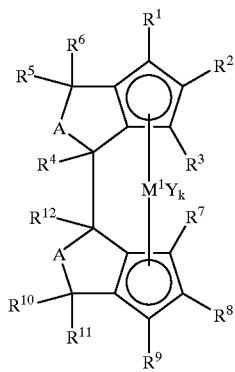

(I)

wherein
M¹ is titanium or zirconium,
Y are identical and are methyl, phenyl or chlorine,
$R^1$, $R^2$, $R^3$, $R^7$, $R^8$ and $R^9$ are identical or different and are each a hydrogen atom, a $C_1$–$C_4$-alkyl group or a $C_6$-aryl group, or $R^1$ and $R^2$ or $R^2$ and $R^3$ or $R^7$ and $R^8$ or $R^8$ and $R^9$ together with the atoms connecting them form an aromatic hydrocarbon ring system,
$R^4$, $R^5$, $R^6$, $R^{10}$, $R^{11}$ and $R^{12}$ are identical or different and are each a hydrogen atom, a halogen atom, a $C_1$–$C_{10}$-hydrocarbon-containing group, an —$SiR^{15}_3$, —$NR^{15}_2$, —$SiOR^{15}_3$, —$SiSR^{15}_3$ or —$PR^{15}_2$ radical, where $R^{15}$ is a halogen atom, a $C_1$–$C_{10}$-alkyl group, or a $C_{6-10}$-aryl group, or two or more radicals $R^4$, $R^5$, and $R^6$ or $R^{10}$, $R^{11}$ and $R^{12}$ together with the atoms connecting them for a ring system, A is 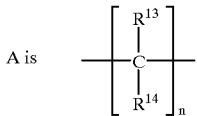

where
$R^{13}$ and $R^{14}$ are identical or different and are each a hydrogen atom, a $C_1$–$C_4$-alkyl group or a $C_6$-aryl group and the transition metal compound of the formula I is not 8,8'-biguaiazulenetitanium dichloride.

2. A transitional metal compound selected from the group consisting of
trans-4,4'-bis(4-phenyl-2,7,7-trimethyl-4,5,6,7-η⁵-tetrahydroindenyl)zirconium dichloride,
trans-4,4'-bis(4-phenyl-2,7,7-trimethyl-4,5,6,7-η⁵-tetrahydroindenyl)zirconium dichloride,
trans-4,4'-bis(2-benzyl-4-phenyl-7,7-dimethyl-4,5,6,7-η⁵-tetrahydroindenyl)zirconium dichloride,
trans-4,4'-bis(4,7,7-trimethyl-4,5,6,7-η⁵-tetrahydroindenyl)zirconium dichloride,
trans-4,4'-bis(2-isopropyl-4,7,7-trimethyl-4,5,6,7-η⁵-tetrahydroindenyl)zirconium dichloride,
trans-4,4'-bis(2-isopropyl-4,7,7-trimethyl-4,5,6,7-η⁵-tetrahydroindenyl)dimethylzirconium,
trans-4,4'-bis(4-phenyl-2,7,7-trimethyl-4,5,6,7-η⁵-tetrahydroindenyl)dimethylzirconium,
trans-4,4'-bis(2-benzyl-4-phenyl-7,7-dimethyl-4,5,6,7-η⁵-tetrahydroindenyl)dimethylzirconium,
trans-4,4'-bis(2-isopropyl-4,7,7-trimethyl-4,5,6,7-η⁵-tetrahydroindenyl)butadienezirconium,
trans-4,4'-bis(4-phenyl-2,7,7-trimethyl-4,5,6,7-η⁵-tetrahydroindenyl)butadienezirconium,
trans-4,4'-bis(2-benzyl-4-phenyl-7,7-dimethyl-4,5,6,7-η⁵-tetrahydroindenyl)butadienezirconium,
trans-4,4'-bis(4-methyl-4,5,6-η⁵-trihydropentalene)zirconium dichloride
trans-4,4'-bis(4-phenyl-4,5,6-η⁵-trihydropentalene)zirconium dichloride
trans-4,4'-bis(4-methyl-6-phenyl-4,5,6-η⁵-trihydropentalene)zirconium dichloride,
trans-4,4'-bis(4-methyl-6,6-diphenyl-4,5,6-η⁵-trihydropentalene)zirconium dichloride,
trans-4,4'-bis(4,6,6-triphenyl-4,5,6-η⁵-trihydropentalene)zirconium dichloride,
trans-4,4'-bis(2-benzyl-4-methyl-4,5,6-η⁵-trihydropentalene)zirconium dichloride,
trans-4,4'-bis(2-isopropyl-4-phenyl-4,5,6-η⁵-trihydropentalene)zirconium dichloride,
trans-4,4'-bis(2,4-dimethyl-6-phenyl-4,5,6-η⁵-trihydropentalene)zirconium dichloride,
trans-4,4'-bis(2-isopropyl-4-methyl-6,6-diphenyl-4,5,6-η⁵-trihydropentalene)zirconium dichloride,
trans-4,4'-bis(2-methyl-4,6,6-triphenyl-4,5,6-η⁵-trihydropentalene)zirconium dichloride,
trans-4,4'-bis(4-methyl-4,5,6-η⁵-trihydropentalene)dimethylzirconium
trans-4,4'-bis(4-methyl-6-phenyl-4,5,6-η⁵-trihydropentalene)dimethylzirconium,
trans-4,4'-bis(2-isopropyl-4-methyl-4,5,6-η⁵-trihydropentalene)dimethylzirconium,
trans-4,4'-bis(4-methyl-4,5,6-η⁵-trihydropentalene)butadienezirconium
trans-4,4'-bis(4-methyl-6-phenyl-4,5,6-η⁵-trihydropentalene)butadienezirconium, and
trans-4,4'-bis(2-isopropyl-4-methyl-4,5,6-η⁵-trihydropentalene)butadienezirconium.

* * * * *

UNITED STATES PATENT AND TRADEMARK OFFICE
CERTIFICATE OF CORRECTION

PATENT NO. : 6,069,264

DATED : May 30, 2000

INVENTOR(S) : Michael Riedel, Gerhard Erker and Martin Könnemann

It is certified that error appears in the above-identified patent and that said Letters Patent is hereby corrected as shown below:

In the abstract, at column 14, at the end of line 8, after "spectroscopy." the following should be added -- $^1$H-NMR (200 MHz, $CD_2Cl_2$): 7.4–7.2 (m, 10H, Ph-H); 7.1–6.6 (m, 6H, Cp-H); 2.7 (m, 2H, $CH_2$); 1.9–0.8 (m, 6H, $CH_2$); 1.3 (s, 6H, $CH_3$); 1.2 (s, 6H, $CH_3$). --;

In column 14, lines 9 through 66 (to the end of column 14) should be deleted.

In the Abstract, the last three lines should be deleted and the following should be inserted:

-- $R^4$, $R^5$, $R^6$, $R^{10}$, $R^{11}$ and $R^{12}$ are identical or different and are each a hydrogen atom, a halogen atom, a $C_1$–$C_{40}$-hydrocarbon-containing group, an —$SiR^{15}_3$, —$NR^{15}_2$, —$SiOR^{15}_3$, —$SiSR^{15}_3$ or —$PR^{15}_2$ radical, where $R^{15}$ is a halogen atom, a $C_1$–$C_{10}$-alkyl group, or a $C_6$–$C_{10}$-aryl group, or two or more radicals $R^4$, $R^5$ and $R^6$ or $R^{10}$, $R^{11}$ and $R^{12}$ together with the atoms connecting them form a ring system, --;

A is

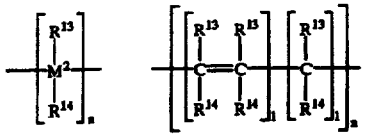

UNITED STATES PATENT AND TRADEMARK OFFICE
CERTIFICATE OF CORRECTION

PATENT NO. : 6,069,264

DATED : May 30, 2000

INVENTOR(S) : Michael Riedel, Gerhard Erker and Martin Könnemann

It is certified that error appears in the above-identified patent and that said Letters Patent is hereby corrected as shown below:

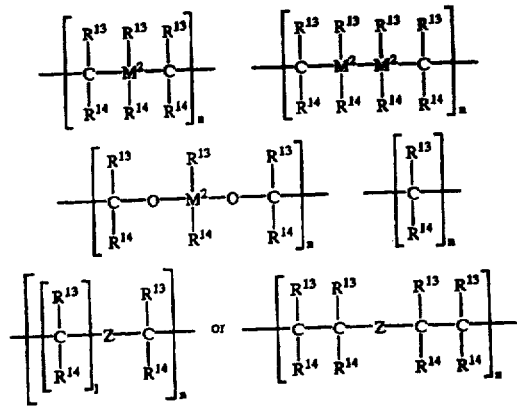

where n is an integer from 1 to 20, l is an integer from 1 to 20, Z is

$SO_2$, O or S, where $R^{15}$ is a halogen atom, a $C_1$–$C_{10}$-alkyl group or a $C_6$–$C_{10}$-aryl group, $R^{13}$ and $R^{14}$ are identical or different and are each a hydrogen atom, a halogen atom or a $C_1$–$C_{40}$-hydrocarbon-containing group or in each case two radicals $R^{13}$, in each case two radicals $R^{14}$, or in each case one radical $R^{13}$ and $R^{14}$, in each case together with the atoms connecting them, form a ring system and $M^2$ is silicon, germanium or tin, and the transition metal compound of the formula 1 is not 8,8'-biguaiazulenetitanium dichloride.

The transition metal compound is suitable as a catalyst component for olefin polymerization.

UNITED STATES PATENT AND TRADEMARK OFFICE
CERTIFICATE OF CORRECTION

PATENT NO. : 6,069,264

DATED : May 30, 2000

INVENTOR(S) : Michael Riedel, Gerhard Erker and Martin Könnemann

It is certified that error appears in the above-identified patent and that said Letters Patent is hereby corrected as shown below:

In claim 1, column 15, line 30, "$C_1$-$C_{10}$" should read -- $C_1$-$C_{40}$ --.

Signed and Sealed this

Tenth Day of April, 2001

Attest:

NICHOLAS P. GODICI

Attesting Officer

Acting Director of the United States Patent and Trademark Office